(12) United States Patent
Mutzel et al.

(10) Patent No.: US 6,686,194 B1
(45) Date of Patent: Feb. 3, 2004

(54) METHOD AND DEVICE FOR SELECTING ACCELERATED PROLIFERATION OF LIVING CELLS IN SUSPENSION

(75) Inventors: Rupert Mutzel, Ander Steig 19, D-78464, Constance (DE); Philippe Marliere, Etiolles (FR)

(73) Assignees: Institut Pasteur, Cedex (FR); Rupert Mutzel, Constance (DE)

( * ) Notice: Subject to any disclaimer, the term of this patent is extended or adjusted under 35 U.S.C. 154(b) by 0 days.

(21) Appl. No.: 09/857,226

(22) PCT Filed: Dec. 2, 1999

(86) PCT No.: PCT/EP99/09422

§ 371 (c)(1),
(2), (4) Date: Sep. 10, 2001

(87) PCT Pub. No.: WO00/34433

PCT Pub. Date: Jun. 15, 2000

(30) Foreign Application Priority Data

Dec. 4, 1998 (DE) .......................... 198 56 136

(51) Int. Cl.[7] ................................ C12M 1/36
(52) U.S. Cl. ................ 435/286.5; 435/286.6; 435/294.1; 435/813
(58) Field of Search .................. 435/286.1, 286.5, 435/286.6, 289.1, 294.1, 813

(56) References Cited

U.S. PATENT DOCUMENTS

| | | | |
|---|---|---|---|
| 2,147,271 A | | 2/1939 | Schwarz et al. ............ 195/141 |
| 5,242,593 A | | 9/1993 | Oberkofler et al. ......... 210/606 |
| 5,316,905 A | * | 5/1994 | Mori et al. .................... 435/3 |
| 6,127,141 A | * | 10/2000 | Kopf ............................ 435/41 |
| 6,271,027 B1 | * | 8/2001 | Sarem et al. ............... 435/325 |

FOREIGN PATENT DOCUMENTS

| | | |
|---|---|---|
| DE | 43 31 409 C1 | 9/1993 |
| DE | 195 01 350 C1 | 1/1995 |
| EP | 0 620 273 A1 | 3/1994 |
| FR | 1 064 614 | 6/1950 |
| JP | 59-173086 | 9/1984 |

OTHER PUBLICATIONS

"Selected Low–Cohesion Variants of Actinobacillus–Actinomycetemcomitans and Haemophilus–Aphrophilus Lack Distinct Antigens Recognized by Human Antibodies", by C. Wyss, *Archives of Mcorbiology*, 1989.

* cited by examiner

Primary Examiner—David A. Redding
(74) *Attorney, Agent, or Firm*—Westman, Champlin & Kelly, P.A.

(57) ABSTRACT

The present invention relates to a method and a device for selecting accelerated proliferation of living cells in suspension. The culture apparatus (2) of the present invention enables cells to proliferate in suspension over unlimited periods of time. Natural selection results in the accumulation of genetic variants which are increasingly better adapted to the chosen culture conditions. The organisms used can be prokaryotic or eukaryotic. The organisms used can be naturally occurring organisms or genetically modified organisms. The culture apparatus of the present invention is also suitable for using continuous, periodical or conditional culture conditions. The physical and chemical characteristics of the culture media used can be chosen by the user. The requirement that a population of cells proliferates exclusively in suspension in continuous culture conditions is satisfied by the periodical transfer of the organism suspension from a first culture vessel into a second culture vessel. After the transfer, the first culture vessel is subjected to a sterilizing treatment and the sterilizing agent is optionally neutralized, so that the first culture vessel is ready for the culture to be transferred back from the second culture vessel. The second culture vessel is then sterilized and neutralized.

24 Claims, 8 Drawing Sheets

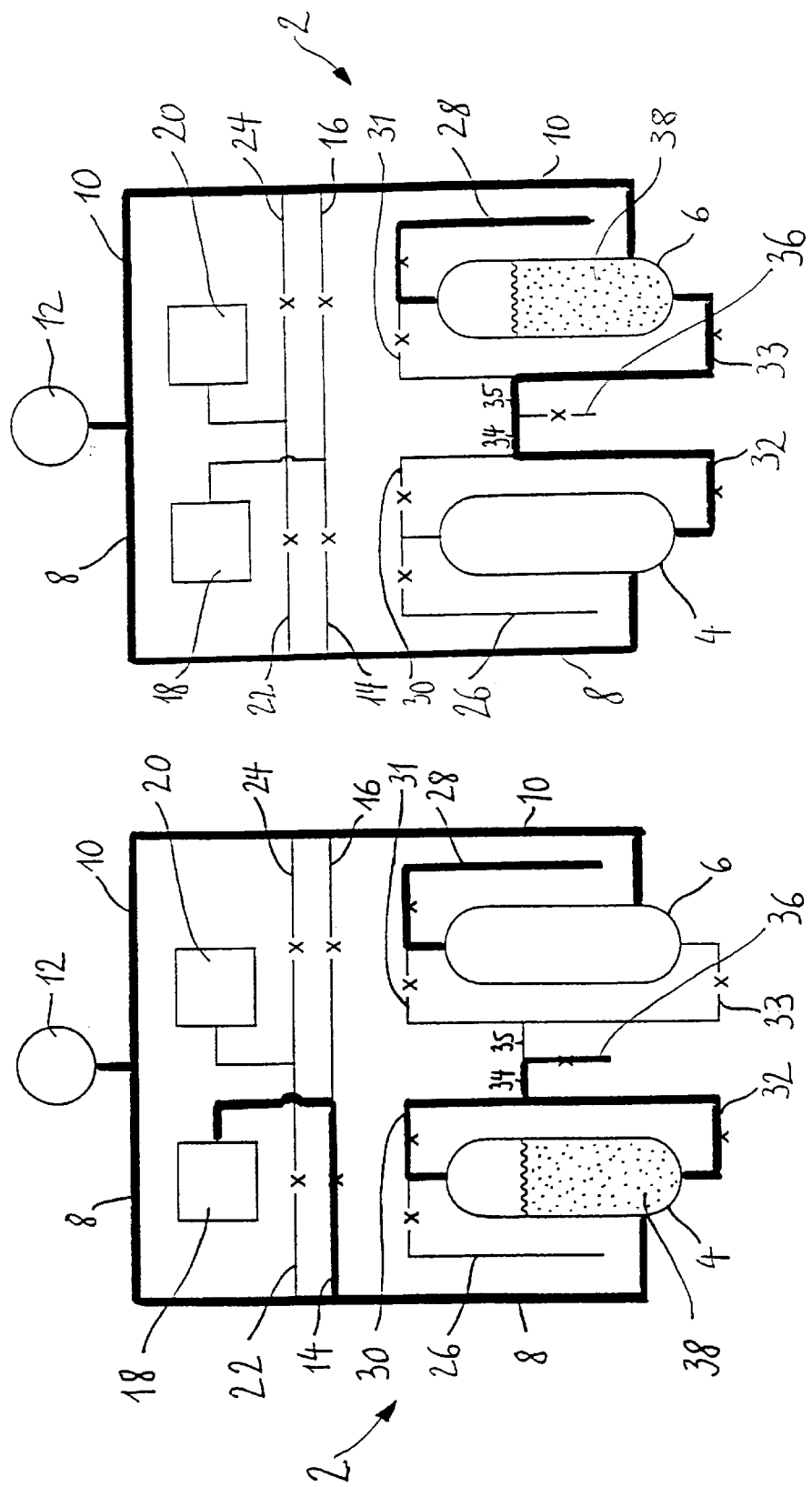

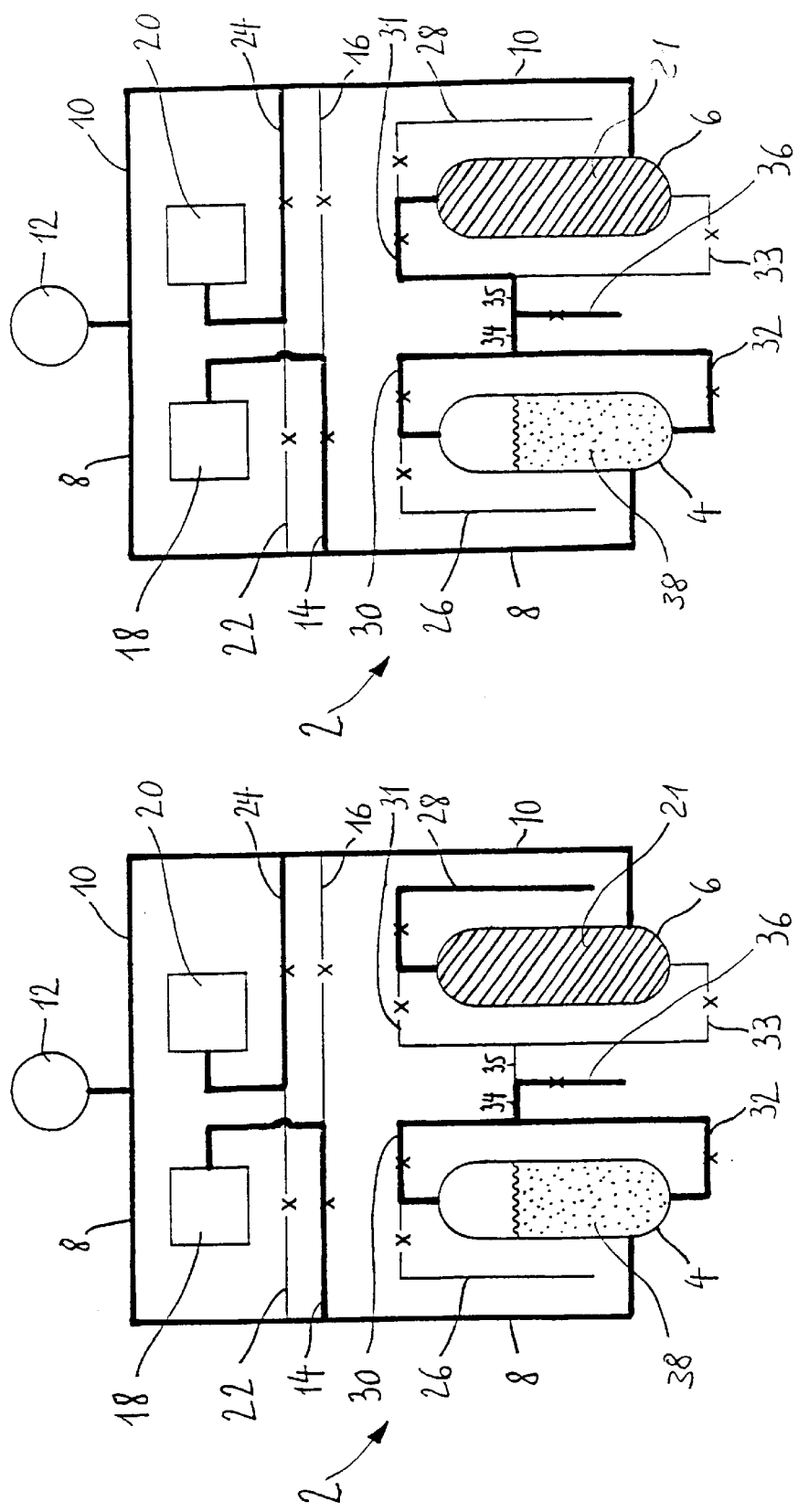

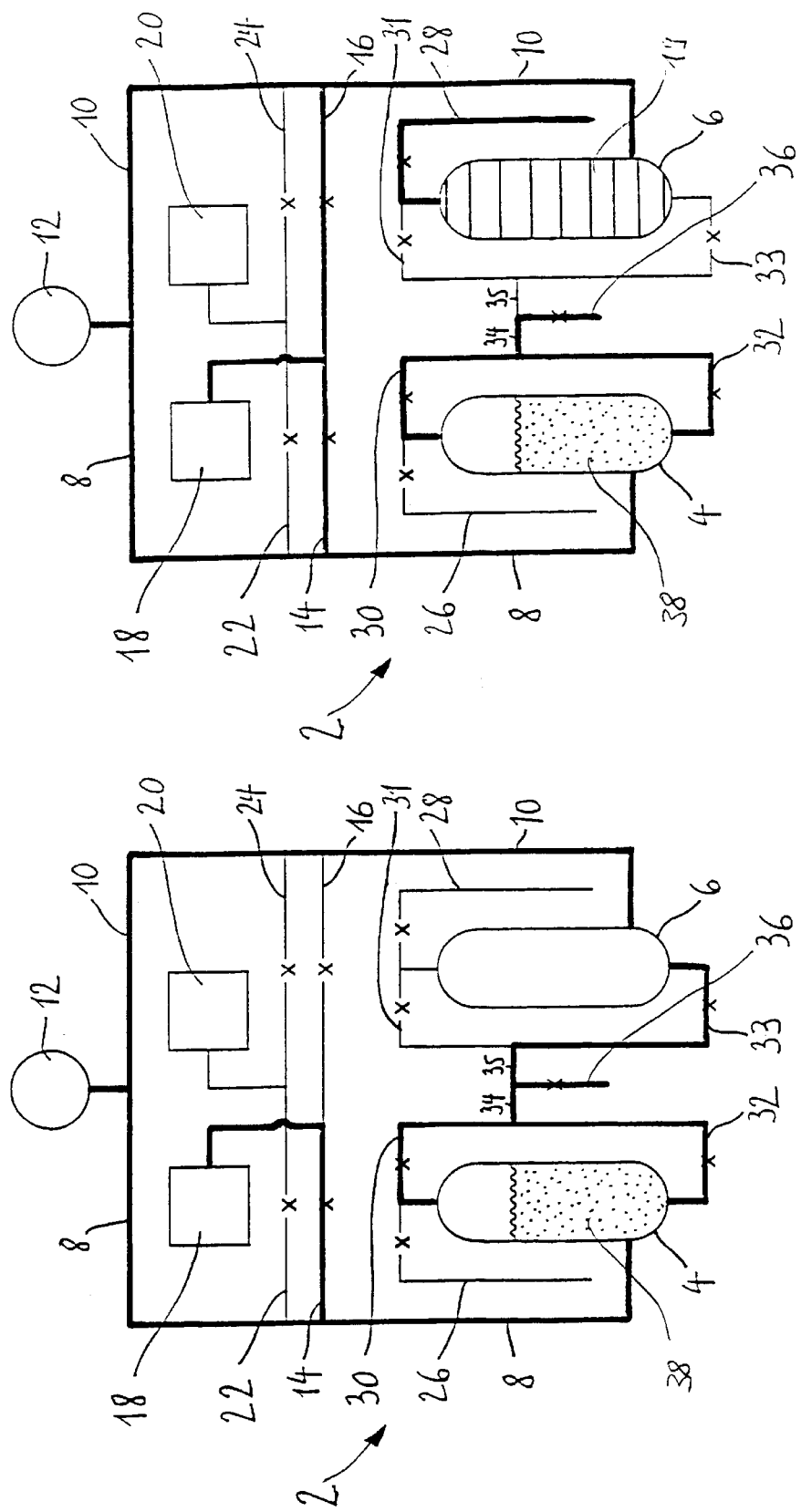

METHOD AND DEVICE FOR SELECTING ACCELERATED PROLIFERATION OF LIVING CELLS IN SUSPENSION

The present application claims priority of German application Serial No. 198 56 136.9, filed Dec. 4, 1998 and International patent application Serial No. PCT/EP99/09422, filed Dec. 4, 1999, and published in German the content of which is hereby incorporated by reference in its entirety.

The present invention relates to a method and a device for selecting accelerated proliferation of living cells in suspension.

Conventionally, it is distinguished between serial and continuous culture methods. In a serial culture technique, culture vessels containing a sterile growth medium are inoculated with a fraction of a culture which was grown under the same growth conditions. This cycle is repeated when the new culture has grown (Lenski, R. E. and Travisano, M. (1994): Dynamics of adaption and diversification: A 10,000-generation experiment with bacterial populations, Proc. Natl. Acad. Sci. USA 91, 6808–6814). The experiments described in the prior art in connection with the proliferation of microbial organisms over the longest time periods were carried out in accordance with this method (Lenski and Travisano, loc. cit.). In continuous culture methods (Dijkuizen, D. E. (1993): Chemostats used for studying natural selection and adaptive evolution, Meth. Enzymol. 224, 613–631) a culture is continuously diluted with a fresh growth medium in accordance with a predetermined regime. In the prior art such experiments are only described to last for limited time periods (Dijkuizen, loc. cit.).

The above-described conventional techniques are in particular disadvantageous in that so far no continuous culture method has been described which ensures the permanent proliferation of organisms in suspension. All described apparatuses select dilution-resistant (static) variants which populate the inner surfaces of the apparatus (Chao, L. and Ramsdell, G. (1985): The effects of wall populations on coexistence of bacteria in the liquid phase of chemostat cultures, J. Gen. Microbiol. 131, 1229–1236). These variants form a subpopulation which escapes the adaptive forces acting on the organisms in suspension. Continuous cultures with constant cell density, such as, e.g., turbidostat are particularly susceptible to an invasion by dilution-resistant variants and can only be carried out over relatively short time periods (about 200 generations). The prior art describes these difficulties but has so far only offered unsuitable solutions thereto. Therefore, such methods are not used in practice for scientific and industrial aims although their potential has been noticed very early (Monod, J. (1950): La technique de la culture continue. Théorie et applications, Ann. Inst. Pasteur 79, 390–410; Novick, A. and Szilard, L. (1950): Description of the chemostat, Science 112, 715–716). In the serial culture, which can be described as the periodical renewal of the culture apparatus—in the present case a simple culture vessel—the invasion with such dilution-resistant variants is avoided. However, it involves much work, i.e. many people are required and, due to the repeated manipulation under conditions which require absolute sterility, this culture is susceptible to contamination (Lenski and Travisano, loc. cit.). Robotization of the serial culture in a sterile environment could reduce these risks. However, it would be bought at the price that a large number of culture vessels are needed, and it would be limited since the mechanical precision of the robot and the sterile environment have to be maintained.

It is therefore an object of the present invention to provide an improved method and an improved device for selecting accelerated proliferation of living cells in suspension. This object is achieved with the features of the claims.

In achieving this object, the invention starts out from the basic idea that the device keeps a suspension of cells in continuous proliferation. A dilution-resistant variant must not be allowed to accumulate in any part of the apparatus. Its function is assured by controlling streams of liquid (fluidics). Under the prerequisite that the regular delivery of liquids, such as, e.g., nutrient media and washing solutions and a continuous supply with sterile gases, such as, e.g., air is assured, the apparatus must operate autonomously over an unlimited time period. Different culture regimes, such as, e.g., chemostat or turbidostat can be applied. If necessary, particular components of cells can be separated or isolated due to the effect of suitable solutions. If necessary, a plurality of these apparatuses can be combined with each other such that the content or part of the content of one apparatus can be transferred into another apparatus.

The requirement that under continuous culture conditions a population of cells only proliferates in suspension is concretely fulfilled by a preferably periodical transfer of the organism suspension from a first culture vessel into a second culture vessel. After the transfer, the first culture vessel has to undergo a sterilizing treatment, if necessary the sterilizing agent is neutralized, and the first culture vessel is then again ready for receiving the culture being transferred back from the second culture vessel, which is subsequently sterilized and neutralized.

This course of actions makes sure (i) that the population of organisms in suspension is maintained at any time and (ii) that all dilution-resistant variants in any part of the apparatus are destroyed during any one of the cycles.

The method of an alternating sterilization of the culture vessels preferably selects directly and regularly against variant organisms which populate the surfaces in the apparatus and avoids the proliferation and adaption of a static, dilution-resistant population. Any device for a continuous culture of organisms can be regarded as an apparatus in which the natural selection prefers mutants which resist dilution. The only possibility which the described method offers the cultivated population for withstanding dilution is an increase in the proliferation rate in suspension. In contrast to a fermentation method, the present invention describes an automated genetics method which simultaneously selects against static variants and prefers dynamic variants which are always better adapted to the culture conditions.

Thus, it is a particular advantage of the present invention vis-à-vis the prior art that a regime with a constant cell density (turbidostat) can be maintained over unlimited time periods and that the growth rate of naturally occurring cells or genetically modified cells can be increased. An example for an industrial application is the enrichment of natural variants being capable of metabolizing a chemical product (such as, e.g., an intermediate product of a chemical synthesis or an environmental pollutant). A further application would be the improvement of an enzyme or a metabolic pathway: if the conversion of a substrate into a product is the limiting step in the metabolism of a cell, and if the cell can be provided with a surplus of this substrate, under the described conditions the continuous culture will lead to an increase in the growth rate which results from an increased turnover rate of the substrate, and this increased turnover rate results from the fixation of the successive mutations in the gene or the genes for the enzymes which are subject to selection for the required turnover of the substrate.

It is a further advantage of the present invention that a plurality of different growth media can be supplied to the organism suspension by the apparatus. This makes it possible to carry out a multiple or alternating adaptation and to diversify the metabolic capacity of the cultivated organisms. A predetermined cell density can be made dependent on variables other than the supply of fresh medium. The fact that this density is reached can condition the effect of chemical and physical agents whose toxicity is adjusted such that the population of the organisms is always at its tolerance limit or that increasingly resistant variants are selected.

Moreover, due to the supply of detergents or solvents, certain components of cells can be extracted. In particular, genetic material such as plasmids or viruses can be extracted automatically, wherein the host cells are destroyed. However, particular agents which make the cells competent for genetic transformations or infections with naturally or synthetically produced nucleic acids can be supplied. This genetic material can then be introduced into the population. In very general terms, two or more apparatuses can be connected with each other. Thus, different organisms can be automatically brought in contact with each other and very different genetic materials such as, e.g., conjugative episomes, phages, transposons, etc. can be automatically introduced.

In the following the present invention is exemplarily explained on the basis of a preferred embodiment, thereby referring to the drawings in which FIG. 1 shows a device according to the invention for selecting accelerated proliferation of living cells in suspension in a starting position in which the cell suspension is contained in a first culture vessel;

FIG. 2 shows the device of FIG. 1 in which the cell suspension is contained in a second culture vessel;

FIGS. 10–16 show the correspondingly reversed course of actions for transferring the culture from the second culture vessel into the first culture vessel.

Figure 3:
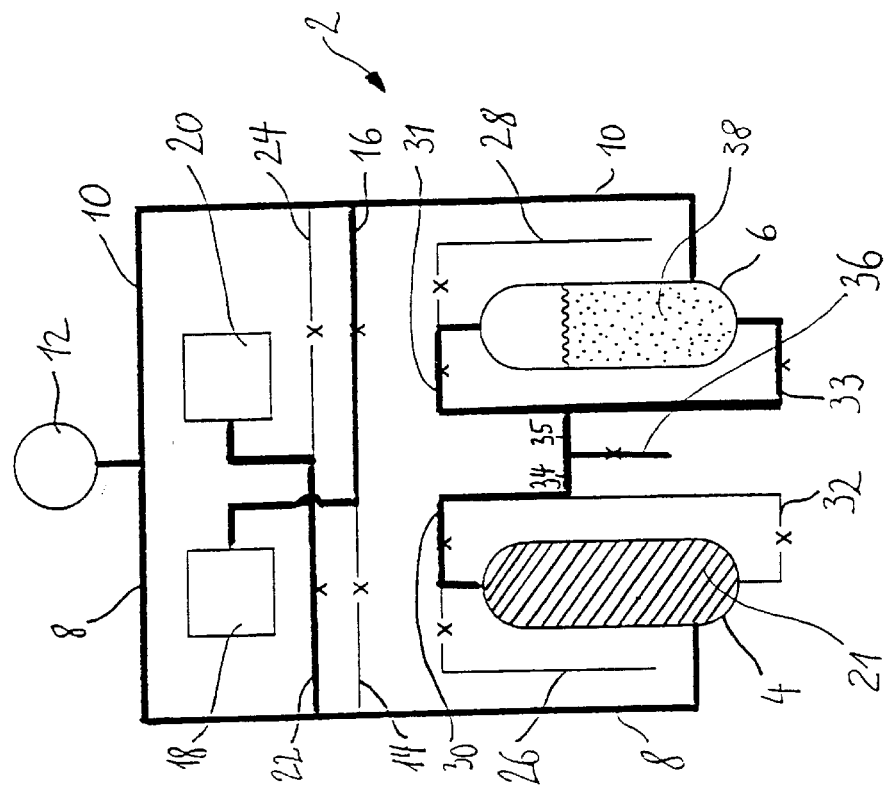
FIG. 3 shows the device of FIG. 2 in which the first culture vessel contains a sterilizing agent.

The device shown in FIGS. 1 to 16 for selecting accelerated proliferation of living cells in suspension can also be called a culture apparatus 2. The culture apparatus 2 allows the proliferation of cells in suspension over unlimited periods of time. Due to the natural selection, genetic variants which are increasingly better adapted to the selected culture conditions are enriched. The used organisms can be prokariotic or eukariotic. Moreover, the organisms used can be naturally occurring organisms or genetically modified organisms. Continuous (Kubitschek, H. E. (1970): Introduction to research with continuous cultures, Prentice-Hall; Pirt, S. J. (1975): Principles of microbe and cell cultivation, Blackwell), periodical (Pirt, loc. cit.) or conditional (Bryson, V. (1952): The turbidostatic selector—a device for automated isolation of bacterial variants, Science 116, 48–51; Fraleigh, S. P., Bungay, H. R. and Clesceri, L. S. (1989): Continuous culture, feedback and auxostats, TIBTech. 7, 159–164) culture conditions can be used. Physical and chemical characteristics of the culture media used can be selected by the user.

The design and the functioning of the culture apparatus 2 are described in the following on the basis of FIGS. 1 to 16. The culture apparatus 2 comprises in particular a first culture vessel 4 and a second culture vessel 6. The two culture vessels 4 and 6 are connected with a pressurized gas supply 12 via conduits 8 and 10, respectively, which preferably mount into the lower portions of the culture vessels 4 and 6, respectively. Moreover, via conduits 14 and 16 the culture vessels 4 and 6 are connected with a medium source 18 which is pressurized as well. The conduits 14 and 16 preferably extend from the medium source 18 and mount into respective conduits 8 and 10, in order to connect the gas supply 12 with the two culture vessels 4 and 6, respectively. Moreover, a pressurized source 20 for a sterilizing agent 21 (e.g. NaOH) is provided, said source 20 being connected with the culture vessels 4 and 6 via conduits 22 and 24, respectively. Preferably, the conduits 22 and 24 mount into the conduits 8 and 10, as described above in connection with conduits 14 and 16.

Moreover, outlet conduits 26 and 28 are provided on the culture vessels 4 and 6, respectively, in order to discharge surplus sterilizing agent 21 or washing solutions 19 during sterilization and neutralization of the respective culture vessel 4 or 6. In addition, connection conduits 30, 31, 32 and 33 are provided between the two culture vessels 4 and 6 in order to connect the two culture vessels 4 and 6 with each other. Preferably, at least two of these connection conduits have a common portion 34 and 35 in which an outlet conduit 36 is provided, said outlet conduit 36 being used for completely emptying one of the two culture vessels 4 or 6 or for discharging the culture 38 or part thereof.

For controlling the method of the present invention for selecting accelerated proliferation of living cells in suspension, the conduits or conduit portions 14, 16, 22, 24, 30, 32, 33, 34, 35 and 36 comprise valves (schematically shown). The valves can, for example, be applied mechanically or, however, they can be controlled electrically or electronically, preferably automatically by using a control means which is not shown.

On the basis of FIGS. 1 to 16, the functioning of the method of the present invention using the above-explained culture apparatus 2 is explained in more detail in the following. It is pointed out in this connection that closed conduit portions are shown as thin lines, whereas conduit portions or conduits through which liquid can flow or is flowing are shown as thick lines. The valves are only shown schematically so that from the manner how they are shown it should not be concluded which kind of valve is used. Moreover, the conduit diagram and the valve arrangement are only schematic. Suitable valves and the best possible conduit connections and valve arrangements can vary depending on the kind of application.

FIGS. 1 to 16 show the most important successive steps in the cultivation/sterilization cycle. According to FIG. 1, the cell suspension is in the first culture vessel under a predetermined culture regime (chemostat, turbidostat). The valves are controlled such that the first culture vessel 4 is connected both with the gas supply 12 and the medium source 18 so that liquids such as, e.g., nutrient media and washing solutions are regularly delivered to the culture 38 and a continuous supply with sterile gases, such as, e.g., air is assured. The connection between the first culture vessel 4 and the source 20 for the sterilizing agent 21 is interrupted by the respective valve. The second culture vessel 6 is connected with the gas source 12. Via the conduit 36 the culture 38 or parts thereof can be discharged.

According to FIG. 2 the culture 38 was transferred via conduits 32, 34, 35 and 33 into the second culture vessel 6, wherein the opening of the conduit 28 guarantees a pressure compensation. All conduits leading from the medium source 18 and the source 20 for the sterilizing agent to the culture vessels 4 and 6 are closed.

In the situation shown in FIG. 3, the first culture vessel 4 was filled with the sterilizing agent 21 after the conduits 32, 34, 35 and 33 had been closed and the conduits 22 and 26 had been opened; a surplus of sterilizing agent 21 is discharged via the outlet conduit 26. After the connection 16 between the medium source 18 and the culture vessel 6 is made, and after the conduit 28 is closed and the conduit portions 31, 33, 35 and 36 are opened, the culture 38 in the second culture vessel 6 can again be supplied regularly with medium.

Figure 4:
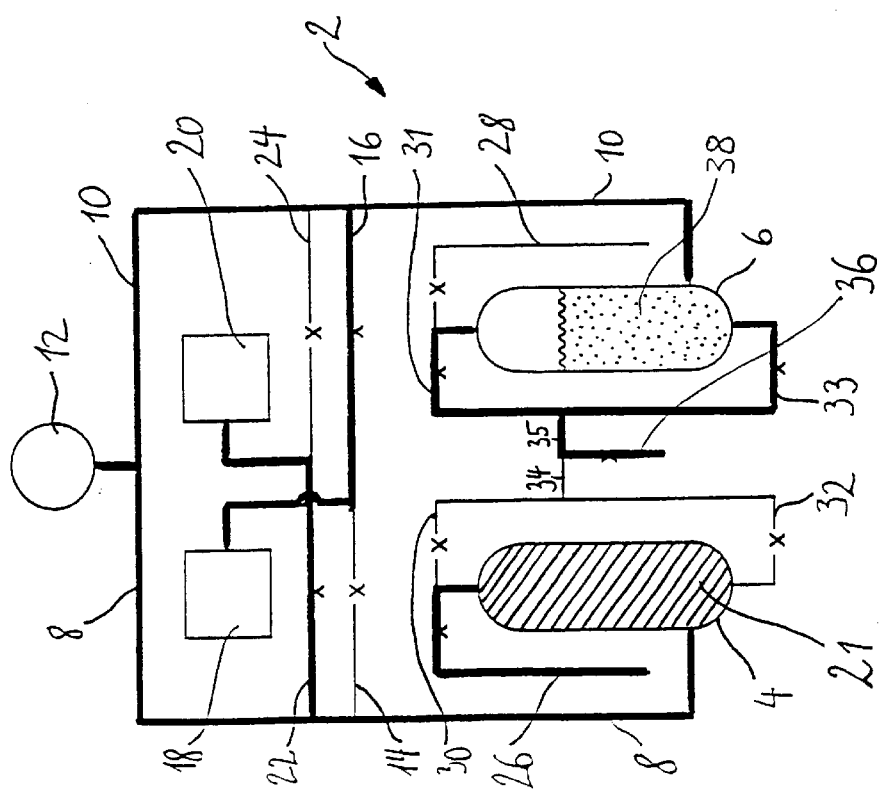
FIG. 4 shows the sterilization of individual conduit portions.

FIG. 4 shows the sterilization of the conduits 30, 34 and 36 by means of a sterilizing agent 21, after the respective conduit portions were opened and the outlet conduit 26 was closed.

Figure 5:
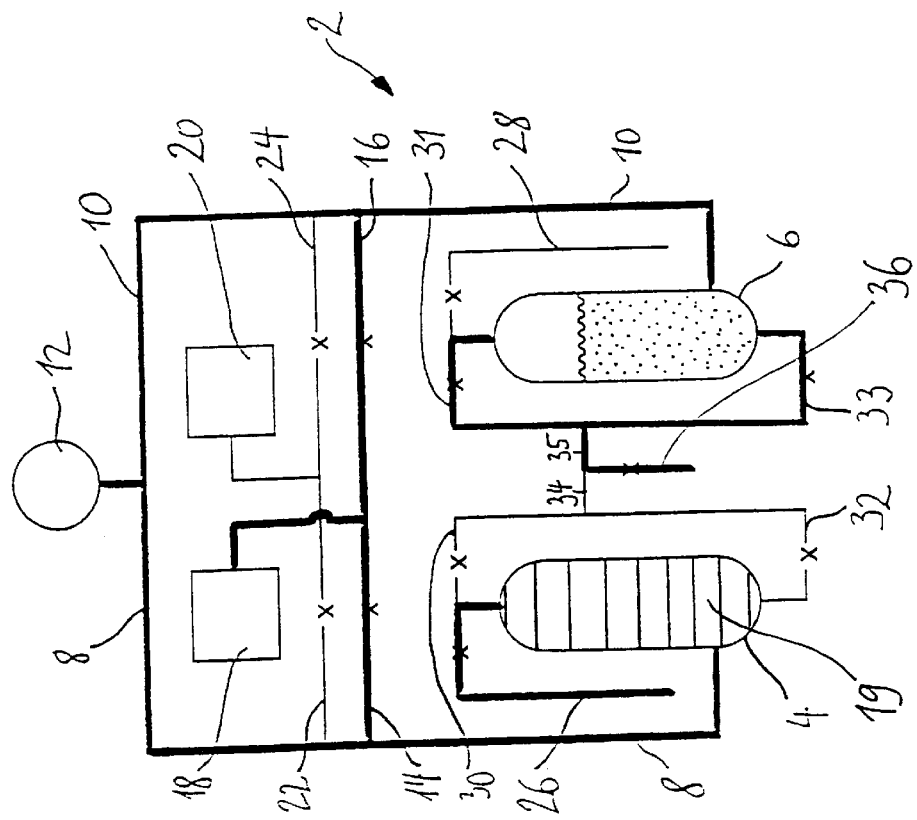
FIG. 5 shows the device during removal of the sterilizing agent from the first culture vessel as well as the respective conduit portions.

In accordance with FIG. 5, the sterilizing agent 21 is now removed from the first culture vessel 4, after the conduits 22, 26 and 33 were closed and the conduit 32 was opened.

Figure 6:
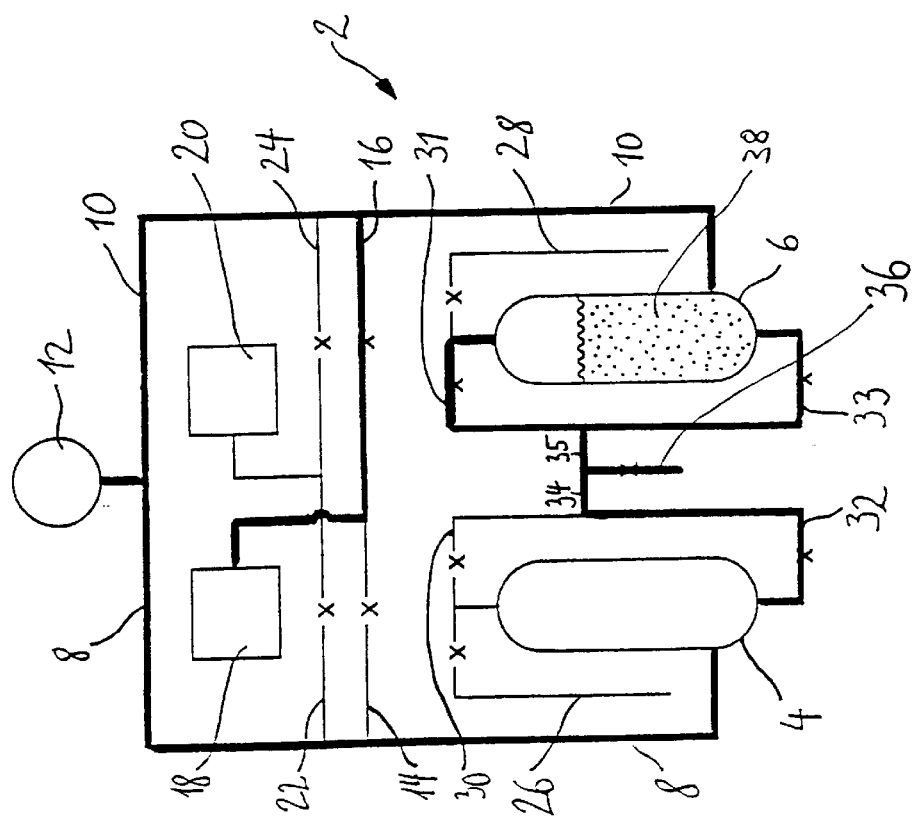
FIGS. 6–8 show steps for removing and neutralizing residues of the sterilizing agent from the first culture vessel and the respective conduit portions with a washing solution.
Figure 7:
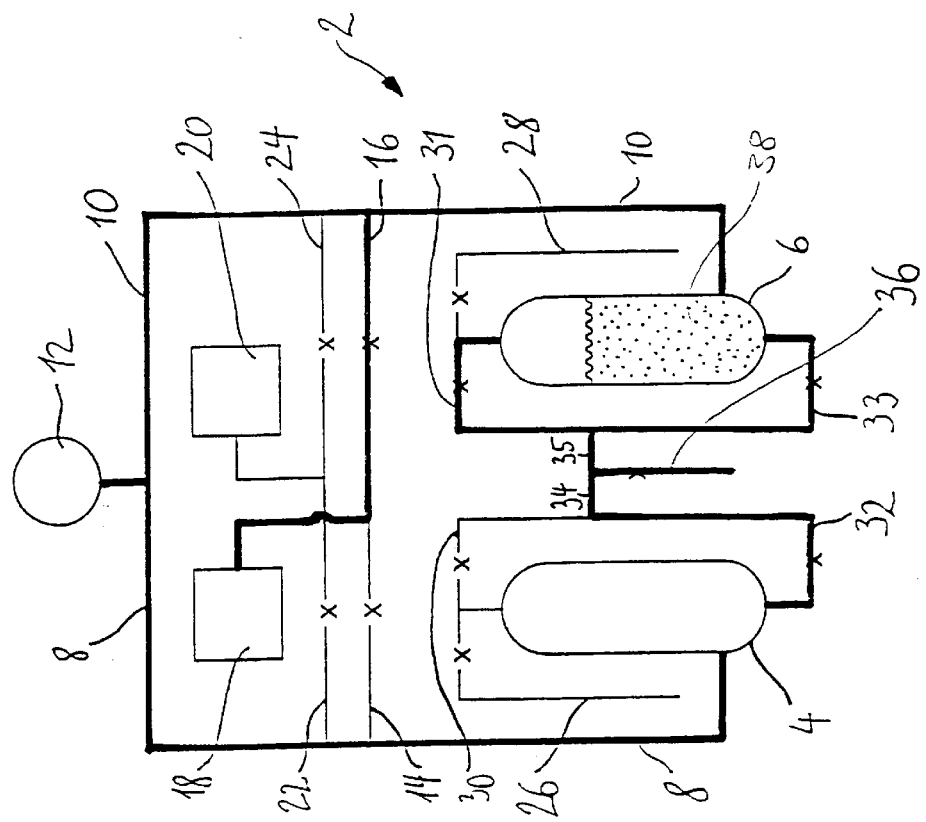
Figure 8:
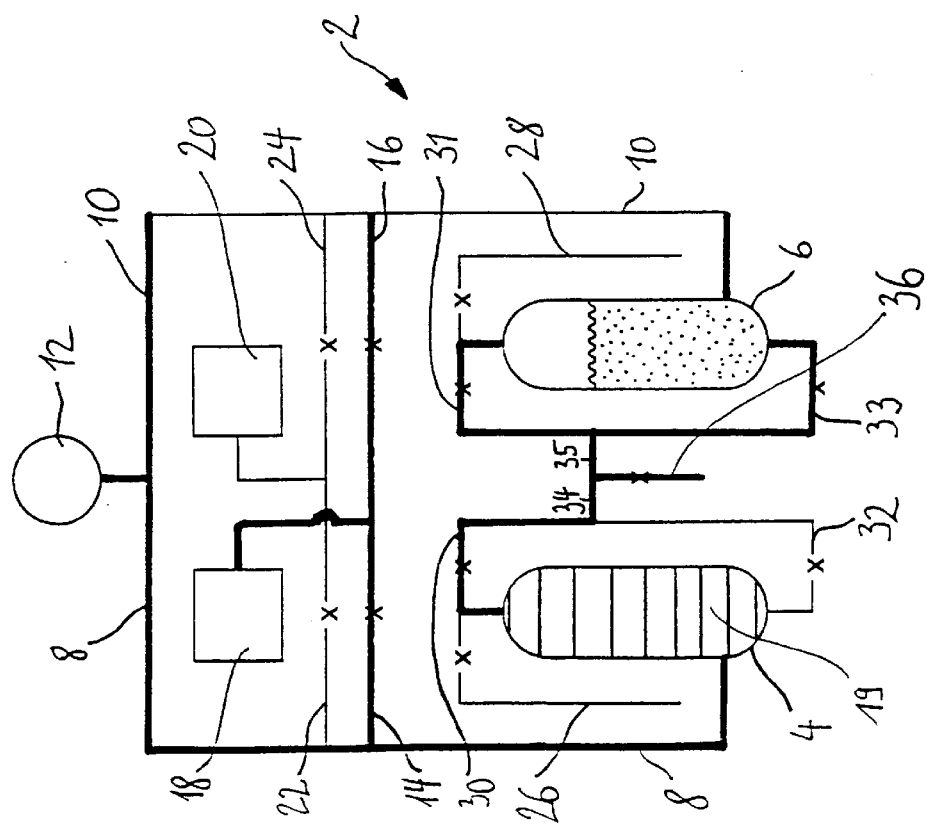

FIGS. 6 to 8 show preferably optional steps for removing and neutralizing possibly remaining residues of the sterilizing agent 21 from the first culture vessel 4 and the respective conduit portion by means of fresh medium:

In FIG. 6 the first culture vessel 4 is filled with medium by opening the conduit 14, after the conduits 32 and 36 were closed and conduit 26 was opened; surplus medium is discharged via the conduit 26. Analogously to the situation in FIG. 4, the conduits 30, 34 and 36 are now flushed with medium (FIG. 7) and, analogously to the situation in FIG. 5, the medium is consequently removed from the culture vessel (FIG. 8).

After opening the conduit 26 and closing the conduits 32 and 34 of the culture vessel 4, there is a situation which is mirror-symmetrical to the situation shown in FIG. 1, wherein the cell suspension is now contained in the second culture vessel 6. The culture 38 or parts thereof can be discharged via the conduit 36.

Figure 10:
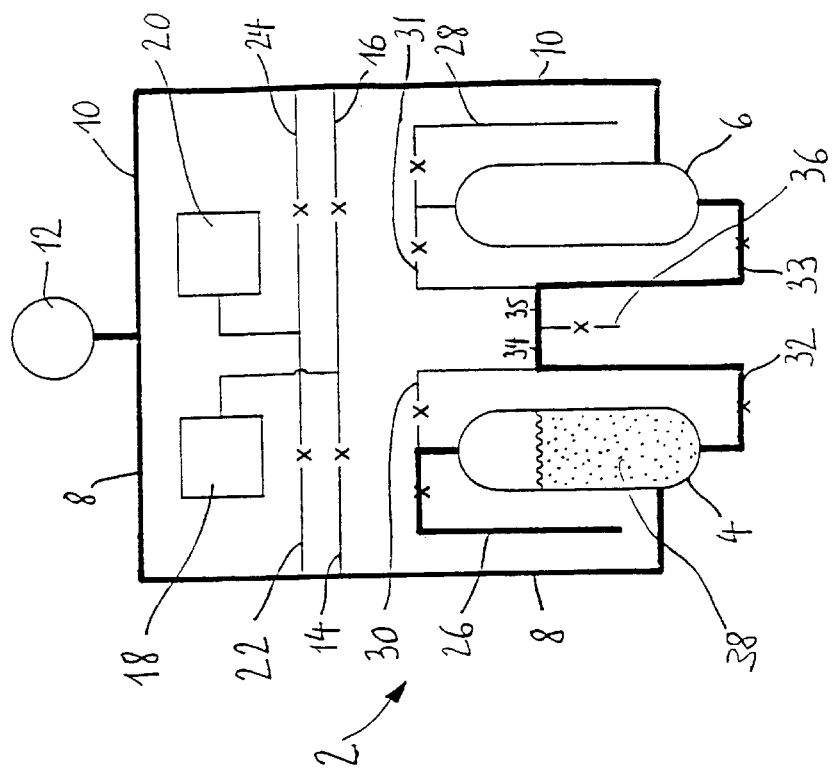
Figure 9:
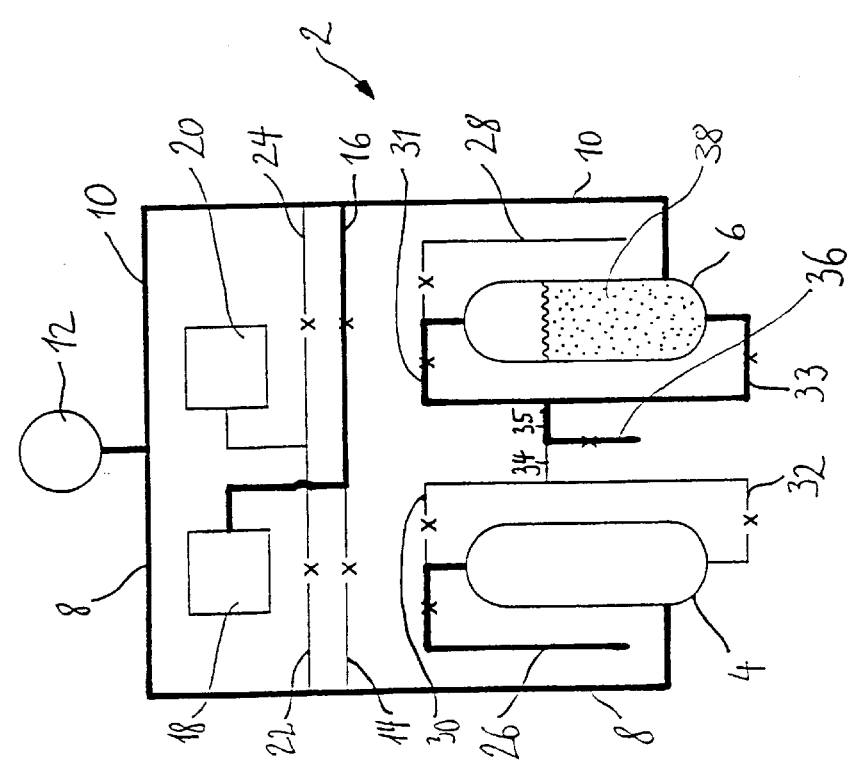
FIG. 9 shows the device of FIG. 3 in which the first culture vessel and the respective conduit portions are sterilized and neutralized.
Figure 15:
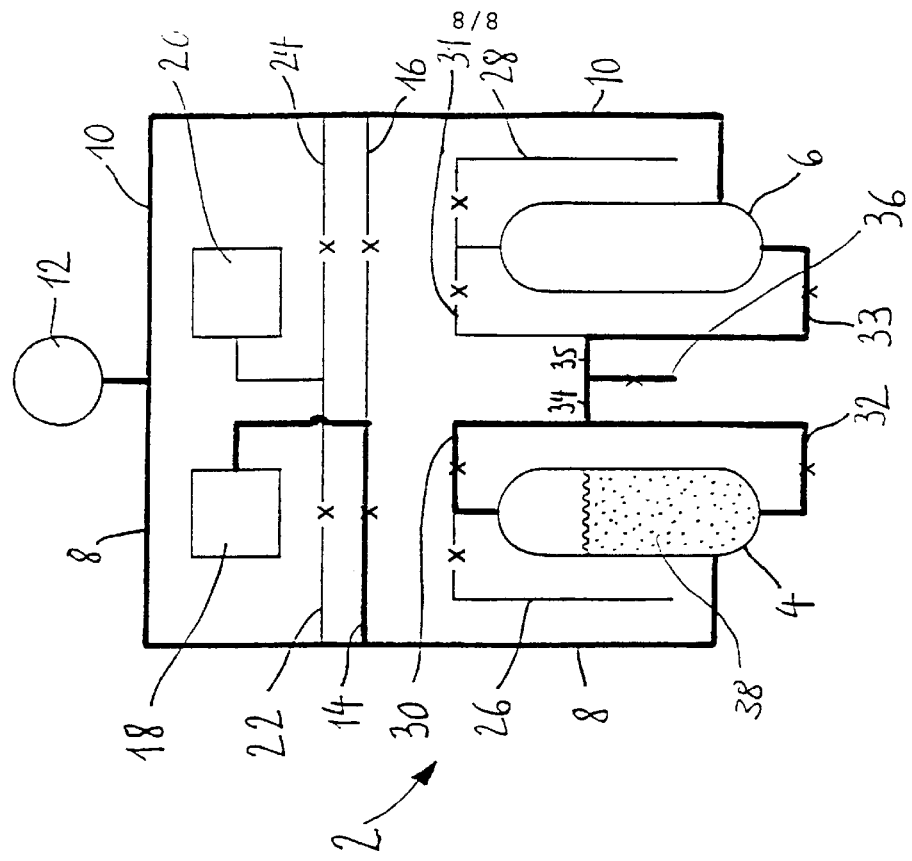
Figure 16:
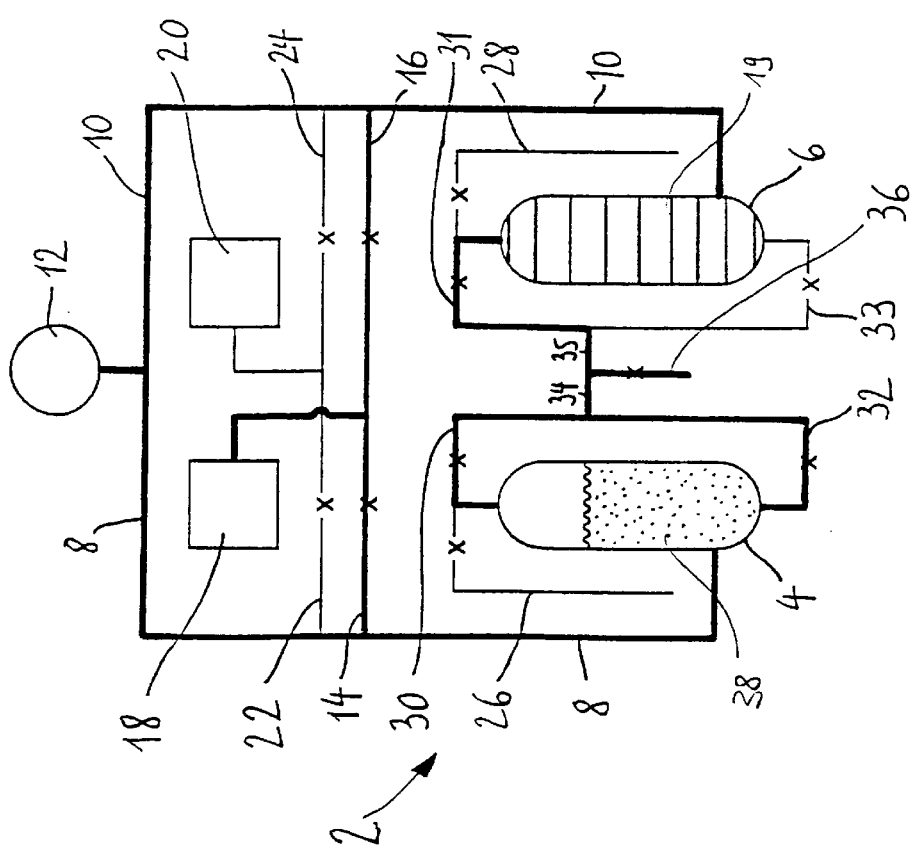

FIGS. 10 to 16 represent the respective symmetrical steps for returning to the starting situation in FIG. 1, i.e.: FIG. 10 shows that the culture 38 is transmitted back from the second culture vessel 6 into the first culture vessel 4; FIG. 11 shows the sterilization of the second culture vessel 6 by means of a sterilizing agent 21; FIG. 12 shows the sterilization of the conduit portions 31, 35 and 36; FIG. 13 shows the removal of the sterilizing agent 21 via the conduit portions 33, 35 and 36; FIG. 14 shows the washing of the culture vessel 6 and the outlet conduit 28 with fresh medium; FIG. 15 shows the washing of the conduits 31, 35 and 36 by means of fresh medium; and FIG. 16 shows the removal of the used medium via the conduits 33, 35 and 36. When the conduit 14 is opened towards the culture vessel 4, the conduits 30 and 34 are opened and the conduit 26 is closed, and the conduit 28 is opened and the conduit portions 33 and 35 are closed, the starting situation of FIG. 1 is restored.

It is pointed out that it is guaranteed that at any point of time of the above-described method at which the sterilizing agent does not flow through the output conduit 36, the culture 38 can be discharged through the respective connection portion and the output conduit 36.

Moreover, the present invention is not limited to the use of two culture vessels 4 and 6 but also more culture vessels can be arranged, e.g., they can be connected in series and/or in parallel so that a plurality of first culture vessels $4_i$ and a plurality of second culture vessels $6_i$ are present.

In a further embodiment of the present invention it would be possible to provide a further culture vessel in addition to the first and second culture vessels in order to temporarily store, e.g., an already used sterilizing agent 21 which could, however, be used again. Also for probable intermediate steps it would be conceivable to provide a further culture vessel.

What is claimed is:

1. A device for selecting accelerated proliferation of living cells in suspension comprising:
   (a) at least a first and at least a second culture vessel for receiving a culture;
   (b) a gas source;
   (c) a medium source;
   (d) a source for a sterilizing agent;
   (e) a conduit system for connecting said gas source with said culture vessels and comprising means for selectively connecting said two culture vessels with said medium source or with said source for said sterilizing agent, wherein the conduit system for supplying gas, medium and/or sterilizing agent into the individual culture vessels each have a common portion; and
   (f) means for connecting said two culture vessels with each other via two connection conduits having a common conduit portion.

2. The device according to claim 1, wherein said means for selectively connecting are valves.

3. The device according to claim 1, wherein said common conduit portion is arranged on a level between the highest and lowest point of said two culture vessels.

4. The device according to claim 3, wherein said common conduit portion has an outlet conduit through which said cultures can be discharged from said culture vessels.

5. The device according to claim 3, wherein said conduit portions form a siphon trap.

6. The device according to claim 3, wherein one of said connection conduits is connected to a lower portion of said culture vessels and said other one of said connection conduits is connected to an upper portion of said culture vessels.

7. The device according to claim 1, wherein conduits from said medium source and/or conduits from said source for said sterilizing agent mount into a conduit which is allocated to said respective culture vessel and extends from said gas source.

8. The device according to claim 1, wherein the conduits of the conduit system which are connected with said gas source, said medium source and/or said source for the sterilizing agent are pressurized.

9. The device according to claim 1, wherein each culture vessel has its own, closable outlet conduit.

10. The device according to claim 9, wherein said outlet conduits mount from the upper portion of said culture vessels and/or branch off from said connection conduit.

11. The device according to claim 1, wherein a plurality of first culture vessels ($4_i$) and/or a plurality of second culture vessels ($6_i$) being arranged in parallel are provided.

12. A method for selecting accelerated proliferation of living cells in suspension comprising the steps of:
    (a) providing a culture in at least one first culture vessel
    (b) continuously supplying said culture in said first culture vessel with gas from a gas source and regularly delivering liquids from a medium source;
    (c) transferring said culture from said first culture vessel via connection conduits into at least one second culture vessel by means of an appropriate conduit connection;

(d) connecting said first culture vessels with a source for a sterilizing agent in order to sterilize said first culture vessel;

(e) removing said sterilizing agent from said first culture vessel;

(f) continuously supplying said culture in said second culture vessel with gas from said gas source and regularly delivering liquids from said medium source;

(g) transferring said culture from said second culture vessel via said connection conduits back into said first culture vessel by means of an appropriate conduit connection;

(h) connecting said second culture vessel with said source for said sterilizing agent in order to sterilize said second culture vessel;

(i) removing said sterilizing agent from said second culture vessel;

(j) optionally repeating steps (b) to (h).

13. The method according to claim 12, wherein said conduit portions being allocated to said respective culture vessel are sterilized by an appropriate conduit connection.

14. The method according to claim 12, wherein residues of said sterilizing agent in said conduit portions or said culture vessel are neutralized after sterilization.

15. The method according to claim 12, wherein at any point of time at which no sterilizing agent is discharged, cultures can be discharged from said culture apparatus.

16. The method according to claim 12, wherein the transfer of said cultures from one culture vessel into said other culture vessel takes place periodically.

17. The method according to claim 12, wherein the transfer of said cultures from one culture vessel into said other culture vessel takes place in such intervals that all cells which populate the conduits are destroyed during any one of these cycles.

18. The method according to claim 12, wherein the transfer of said cultures from one culture vessel into said other culture vessel takes place in such intervals that the population of organism in suspension is maintained at any point of time and all cells which stick to any part of said apparatus are destroyed during any one of these cycles.

19. The method according to claim 12, wherein the conduits are connected by means of valves.

20. The method according to claim 12, wherein the liquid supplied to said culture contains nutrient media and/or washing solutions.

21. The method according to claim 12, wherein said sterilizing agent is at least partially removed through outlet conduits allocated to said culture vessels.

22. The method according to claim 12, wherein at least two of said steps (b) to (h) overlap temporarily or take place at the same time.

23. The method according to claim 12, wherein NaOH is used for the sterilization.

24. The method according to claim 12, wherein the culture is maintained under chemostat conditions or turbidostat conditions.

* * * * *